Jan. 13, 1959 A. KOJAKANIAN Plant Pat. 1,795
PEACH TREE
Filed March 24, 1958
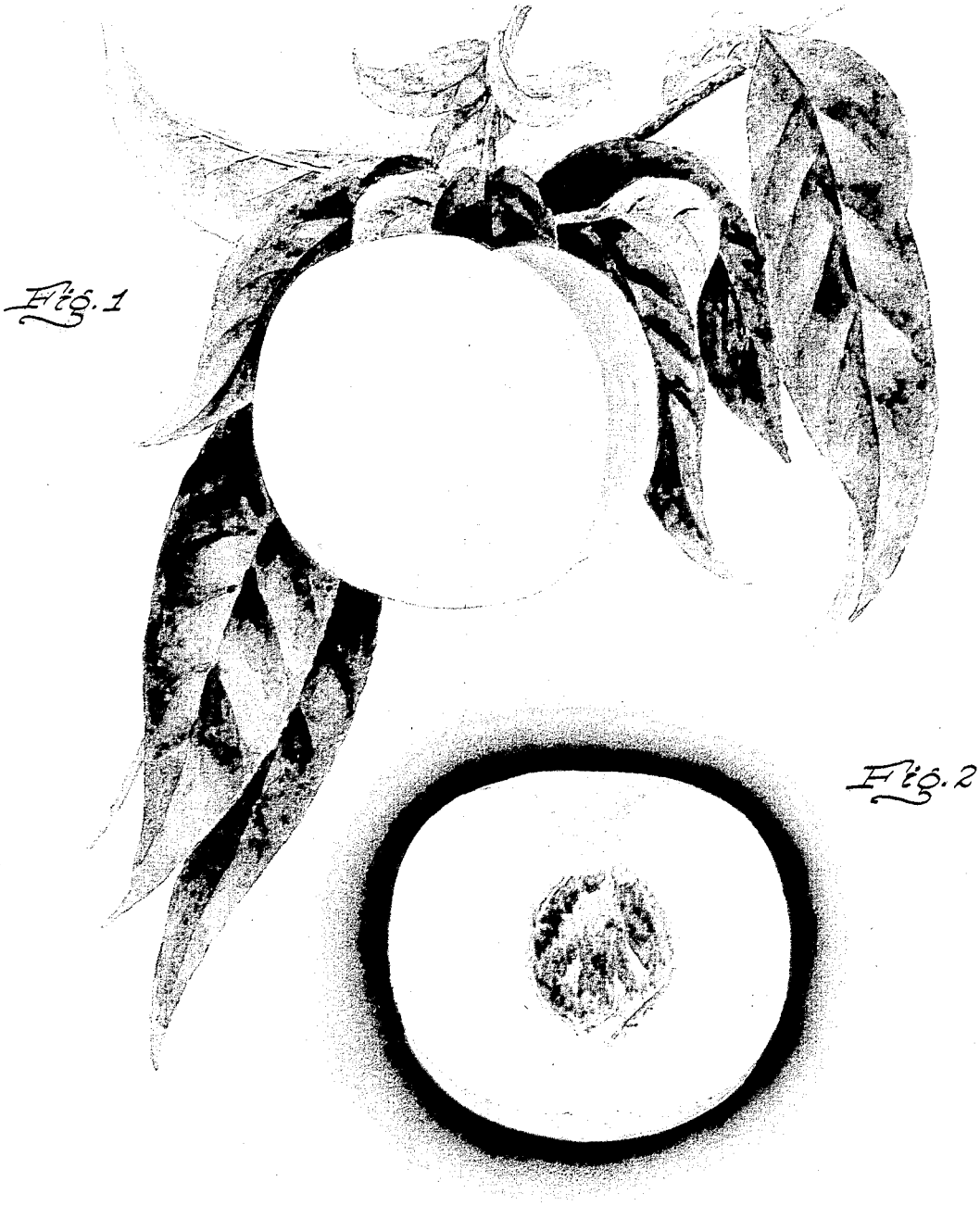
WITNESS
Addison E. Avery
INVENTOR.
Alexander Kojakanian
Webster & Webster
ATTYS.

United States Patent Office

Plant Pat. 1,795
Patented Jan. 13, 1959

1,795

PEACH TREE

Alexander Kojakanian, Modesto, Calif., assignor of one-half to Aram Kojakanian, Modesto, Calif.

Application March 24, 1958, Serial No. 723,618

1 Claim. (Cl. 47—62)

This discovery relates to a new and distinct variety of peach tree which bears relatively large clingstone fruit having yellow skin with an attractive red blush, and yellow flesh shading to red toward the stone; the fruit being of good eating quality, with a distinct and pleasing aroma.

The present variety of peach tree is particularly characterized by a late ripening period, and which is such that fruit is available in the market during approximately the last three weeks of the month of October; such fruit—in comparison to the late ripening Merrill Halloween I peach, United States Plant Patent No. 1,473—being a non-melting clingstone, having more external red color, and a somewhat later maturity.

I discovered the present variety of peach tree growing as a chance seedling in the yard of my ranch located near Modesto, county of Sanislaus, State of California; the area in which the discovery was made being thus subject to my control, continued observation, and cultivation. When such seedling came into bearing I recognized the distinctive nature of the fruit as compared to other existing varieties, and with which I am quite familiar. I therefore selected the variety for subsequent testing, as it evidenced substantial commercial potential, and asexual reproduction for such purpose was accomplished as follows:

The variety was June-budded on root stock for my account, and under my direction, by a commercial nursery, located at Modesto, county of Stanislaus, State of California. Thereafter a number of the trees so reproduced were transplanted to—and grown, under careful observation, upon—my ranch located as aforesaid. When such reproductions grew to maturity, and came into bearing, they ran true to the parent tree in all respects.

In the drawings:

Fig. 1 is an elevation of one of the fruit, together with twigs and leaves.

Fig. 2 is a sectional elevation of one of the fruit, with the stone exposed but having flesh adherent thereto.

Referring now more specifically to the pomological details of this new and distinct variety of peach tree, the following is an outline description thereof; all major color plate identifications being by reference to Maerz and Paul Dictionary of Color, except where common terms of color definition are employed:

Tree:
- *Size.*—Medium.
- *Vigor.*—Medium.
- *Growth.*—Upright—spreading.
- *Density.*—Medium.
- *Form.*—Vase shaped.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Brown.
- *Lenticels.*—Medium number; medium size.

Leaves:
- *Size.*—Medium. Average length, 6½"–7". Average width, 1⅜–2".
- *Form.*—Acuminate. Lanceolate to slightly oval, or ovate-lanceolate.
- *Thickness.*—Medium.
- *Texture.*—Smooth.
- *Margin.*—Glandular; finely serrate.
- *Petiole.*—Medium length; thick.
- *Glands.*—Average number — three (one–four). Tend to be alternate; medium size; reniform; green. Usually positioned one or two basal on blade; one or two apical on petiole.
- *Stipules.*—Dehiscent.
- *Color.*—Top side—medium green (23–L–3). Under side—lighter green (22–J–5).

Flower buds:
- *Hardiness.*—Hardy.
- *Size.*—Small.
- *Length.*—Medium.
- *Form.*—Obtuse; conic; free.
- *Pubescence.*—Pubescent.

Flowers:
- *Blooming period.*—Same as Merrill Fiesta Peach (United States Plant Patent No. 1,099), and Kim Elberta Peach (United States Plant Patent No. 15). Medium compared with other varieties.
- *Size.*—Small.
- *Color.*—Pink.

Fruit:
- *Maturity when described.*—Eating ripe, October 17, 1957.
- *Date of first picking in average season.*—October 10.
- *Date of last picking in average season.*—October 31.
- *Size.*—Uniform. Large—medium. Average diameter axially, 2¾"–3⅛". Average transversely in suture plane, 3" to 3¼".
- *Form.*—Uniform; symmetrical. Truncate—globose.
- *Suture.*—Distinct—shallow. Extends from base to apex, with depression beyond pistil point.
- *Ventral surface.*—Rounded; slightly lipped toward base; lips somewhat unequal.
- *Cavity.*—Abrupt; elongated in suture plane, with suture showing on one side. Average depth, ¾". Average breadth, 1", but somewhat variable. Markings—none.
- *Base.*—Rounded.
- *Apex.*—Short; rounded to truncate.
- *Pistil point.*—Apical.

Skin:
- *Thickness.*—Thin.
- *Toughness.*—Medium.
- *Tenacity.*—Tenacious to flesh.
- *Down.*—Moderate; short; does not roll up when rubbed.
- *Color.*—Yellow (9–K–4 to 9–K–6 to 9–I–8), blushed bright red (2–K–10) shading to medium red (6–K–6), washed one-half to three-fourths over the fruit surface.

Flesh:

*Amygdalin.*—Scant.

*Texture.*—Firm; meaty; non-melting.

*Fibers.*—Few; tender.

*Ripens.*—Even.

*Flavor.*—Mild.

*Aroma.*—Distinct.

*Eating quality.*—Good.

*Color.*—Deep rich yellow (9–J–5) shading to red (2–J–10) toward stone, and streaked with darker red (3–L–3) next to the stone. Surface of pit cavity—red.

Stone:

*Type.*—Cling; adheres to flesh over entire surface.

*Fibers.*—Short.

*Size.*—Medium — large. Average length, 1½″–1 7/16″. Average breadth, 1″–1⅜″ (suture). Average thickness, 13/16″–15/16″ (cheek).

*Form.*—Oval.

*Base.*—Straight.

*Hilum.*—Broad; oval.

*Apex.*—Acuminate.

*Sides.*—Nearly equal.

*Surface.*—Regularly furrowed.

*Ridges.*—Rounded; interrupted.

*Pits.*—Elongated.

*Ventral edge.*—Thick, without wing throughout.

*Dorsal edge.*—Full, with shallow, medium groove throughout.

*Tendency to split.*—Slight.

*Color.*—Dark reddish brown (55–L–7) in freshly cut fruit.

Use: Market; canning.

Keeping Quality: Good.

Shipping quality: Good.

The tree and its fruit herein described may vary in slight detail due to climatic and soil conditions under which the variety may be grown.

The following is claimed:

A new and distinct variety of peach tree, as illustrated and described, characterized by small pink flowers which bloom substantially with the Merrill Fiesta and Kim Elberta, and by relatively large clingstone fruit having yellow skin blushed bright red to medium red over one-half to three-fourths of the fruit surface, and firm, meaty, non-melting yellow flesh shading to red toward the stone, with darker red streaks next to the latter; and further characterized—in comparison with the Merrill Halloween I—by more external red color, the non-melting flesh, and a somewhat later harvest season, the latter normally extending through the last three weeks of October.

No references cited.